United States Patent [19]

Asgar et al.

[11] 3,980,472
[45] Sept. 14, 1976

[54] DENTAL AMALGAM

[75] Inventors: Kamal Asgar; Steven H. Reichman, both of Ann Arbor, Mich.

[73] Assignee: Special Metals Corporation, New Hartford, N.Y.

[22] Filed: July 16, 1975

[21] Appl. No.: 596,399

[52] U.S. Cl. .................................. 75/169; 75/.5 R; 75/134 N; 75/134 C; 75/173 R; 75/173 C
[51] Int. Cl.² ........................................ C22C 7/00
[58] Field of Search ............... 75/.5 R, 169, 173 C, 75/173 R, 134 N, 134 C

[56] References Cited
UNITED STATES PATENTS 3,305,356   2/1967   Youdelis ..................... 75/169 X
3,841,860   10/1974  Wolf ............................ 75/.5 R

*Primary Examiner*—L. Dewayne Rutledge
*Assistant Examiner*—E. L. Weise
*Attorney, Agent, or Firm*—Harness, Dickey & Pierce

[57] ABSTRACT

An improved metal powder blend and improved dental amalgams produced therefrom comprising a mechanical mixture containing controlled proportions of an amalgamatable silver-base alloy powder and a substantially non-amalgamatable eutectic alloy powder containing a controlled quantity of tin which upon trituration with mercury forms a substantially continuous matrix having dispersed therethrough discrete phases of the non-amalgamatable powder particles which impart improved mechanical properties to the resultant dental restoration.

7 Claims, No Drawings

DENTAL AMALGAM

BACKGROUND OF THE INVENTION

Typically, silver-base alloys suitable for forming dental restorations in accordance with American Dental Association specifications nominally contain from about 26% to about 28% tin, about 1% to about 2% zinc, about 2% to about 4% copper, with the balance essentially all silver. Alloys of the foregoing type are provided in a finely-particulated powder form of an average particle size usually less than about 100 microns and are adapted to be triturated by the dentist with about 40% up to about 60% mercury, whereby the ensuing amalgamation reaction effects a hardening of the mixture within a matter of a few minutes during which additional shaping, such as by carving, can be carried out for a period of up to about 15 minutes, and the amalgamation reaction is usually complete within about 24 hours. The general requirements of dental amalgams of the foregoing type include a retention of shape, color and appearance; a biological compatability, a restoration of the tooth to its original function and a long, durable operating life. Extensive investigations and tests conducted on dental restorative materials including dental amalgrams has revealed that creep resistance and compressive strength are particularly important mechanical properties which can be directly correlated to the susceptiblity of such restorations to failure or fracture.

A composition having improved marginal fracture characteristics and other mechanical properties is dislocsed in U.S. Pat. No. 3,305,356, whereby a dental alloy is provided having improved compressive strength and abrasion resistance and decreased flow rate or dynamic creep. In accordance with the teachings of the aforementioned U.S. patent, conventional dental alloys are substantially improved in their mechanical properties by dispersing a controlled quantity of non-amalgamatable alloy particles throughout the conventional amalgam, which comprise a discrete dispersion phase chemically bonded in a substantially continuous matrix composed of the conventional amalgam.

While dental amalgams produced in accordance with the teachings of the aforementioned patent are possessed of improved mechanical properties, including higher compressive strength, thereby better withstanding the mastication forces to which they are subjected, it has been observed that the mechanical properties of such alloys deteriorate with aging of the alloy particles prior to amalgamation, and this deterioration is manifested by a significant reduction in the compressive strength of the resultant amalgam. The loss in compressive strength as a result of the deterioration of the alloy powder prior to amalgamation is at least in part attributable to the presence of voids or cracks in the amalgam along the boundaries between the dispersed phase and the continuous matrix. The presence of such porosity in the amalgam has occasioned premature failure of dental restorations produced therefrom, not only because of the reduced compressive strength, but also because of the poor tensile strength of such restorations, which tend to fracture or break as a result of the imposition of bending stresses thereon during mastication.

The present invention overcomes the problems and disadvantages associated with dental amalgams of the type disclosed in U.S. Pat. No. 3,305,356 by providing a metal powder mixture for use in producing dental amalgams which has improved shelf life and does not deteriorate during storage prior to amalgamation, enabling the attainment of dental restorations of continuous high strength and excellent mechanical properties.

SUMMARY OF THE INVENTION

The benefits and advantages of the present invention are achieved by an alloy powder blend suitable for use in the preparation of dental amalgam for use in dental restorations and the like by trituration with from about 40% to about 60% mercury, and in which the powder particles are of an average particle size less than about 100 microns, and preferably from about 5 microns to about 40 microns in size. The alloy powder blend comprises a mechanical mixture comprised of from about 55% to about 90% of a first powder composed of a silver-base amalgamatable alloy, and from about 10% up to about 45% of a second powder composed of a substantially non-amalgamatable silver-containing alloy which includes a controlled quantity of tin. The amalgamatable powder constituent consists essentially of about 75% silver and about 25% tin, with the silver-tin alloy being replaceable by up to about 5% copper and up to about 2% zinc. The non-amalgamatable powder consists of a silver-containing alloy containing about 1% to about 20% tin, a second alloying constituent individually selected from the group consisting of about 5% cadmium, about 5% to about 50% zinc, about 5% to about 50% aluminum, copper in an amount to provide a silver-to-copper ratio of about 2.6:1, up to 30% indium in combination with copper in an amount to provide a silver-to-copper ratio of about 2.6:1, and with the balance consisting essentially of silver.

In accordance with the preferred embodiments, the non-amalgamatable powder consists of a eutectic silver-copper alloy having a silver-to-copper ratio of about 2.6:1 and containing from about 2% to about 10% tin. Upon trituration with mercury in an amount from about 40% up to about 60%, and preferably from about 46% to about 50% mercury, a high strength amalgam is produced in which the non-amalgamatable particles are substantially uniformly dispersed through a substantially continuous matrix and are chemically bonded therein forming an integral high strength mass of excellent mechanical properties.

Additional benefits and advantages of the present invention will become apparent upon a reading of the description of the preferred embodiments and the specific examples provided.

Description of the Preferred Embodiments

The quantities and proportions of the individual alloying constituents comprising the alloy powder mixture, as well as the resultant dental amalgam prepared therefrom, are herein defined in terms of percentages by weight and on a weight ratio basis unless clearly indicated to the contrary.

The silver-base amalgamatable alloy powder suitable for use in accordance with the practice of the present invention may contain a minimum of about 65% silver, a maximum of about 6% copper, a maximum of about 2% zinc and a minimum of about 25% tin. Alloys containing from about 26% to about 28% tin, from about 1% to about 2% zinc, from about 2 % to about 4% copper and the balance essentially all silver are particularly satisfactory. Amounts of copper in excess of about 6% distributed uniformly through the powder particles are undesirable due to the tendency of dental amalgams incorporating such large amounts of copper to corrode and/or discolor in use.

The non-amalgamatable powder may comprise a high strength silver-containing alloy which preferably comprises a eutectic composition containing from about 1% up to about 20% tin, and preferably from about 2% up to about 10% tin. Among such alloys are a eutectic silver-copper alloy comprised of 72% silver and 28% copper in further combination with the tin alloying constituent, providing a silver-to-copper ratio of about 2.6:1. The aforementioned eutectic silver-copper alloy may further include up to 30% indium in further combination with the tin constituent. Additional alloy compositions suitable for producing the substantially non-amalgamatable powder constituent are silver-cadmium alloys containing 5% to 50% cadmium; silver-zinc alloys containing from 5% to 50% zinc; and silver-aluminum alloys containing 5% to 50% aluminum, with each of the aforementioned alloys containing a controlled amount of tin in an amount of from 2% up to 20%. Of the foregoing alloys, the eutectic silver-copper alloy (72% silver-28% copper) containing from 4% to 10% tin is particularly satisfactory and constitutes the preferred non-amalgamatable powder composition.

The powder particles preferably are of a spherical configuration and of an average size less than 100 microns, with a size range of about 5 microns to about 45 microns being particularly satisfactory. The powder compositions can be readily produced by microcasting a molten mass of the alloy, such as by fluid atomization, gas atomization, airless spraying and centrifugal fragmentation, so as to effect a subdivision of the molten mass into a plurality of fine-sized liquid droplets which are of substantially the same composition. A gas atomization technique which has been found particularly satisfactory for this purpose is described in U.S. Pat. No. 3,253,783, the teachings of which are incorporated herein by reference. Although less desirable, it is also contemplated that powder particles of an irregular shape can be produced by mechanical means, such as by shaving, filing, lathe turning, etc., an ingot of the desired alloy composition which are subsequently screened to recover particles which are within the desired size range.

The gas atomization apparatus, as described in detail in the aforementioned U.S. patent, forms a molten stream of the metal alloy which is atomized in response to the impingement of a conically-shaped vortex of gas, and whereafter the resultant droplets progressively solidify as they fall downwardly through a cooling and collection chamber. In accordance with the preferred practice, a substantially inert gas, such as a substantially dry argon, nitrogen or helium gas, is employed for effecting an atomization of the powder, and also as the cooling medium within the collection chamber, so as to prevent or minimize the formation of undesirable oxides on the particle surfaces. It is also contemplated that air can be employed as the atomization and collection medium, although is is usually preferred to subject the resultant powder produced thereby to a post-treatment in which the powder particles are heated in a reducing atmosphere, such as hydrogen for example, to reduce any oxides present. The collected powder particles are subjected to a preliminary screening operation in which particles of the desired size range are removed and the remainder is recycled.

Appropriate proportions of the amalgamatable and non-amalgamatable powders are blended mechanically to form a substantially uniform mixture in which the non-amalgamatable powder constituent may range from about 10% up to about 45%, and preferably is controlled within a range of about 25% to about 35%. Quantities of the non-amalgamatable powder less than about 10% are usually undesirable due to the relatively low concentration of the discrete phases present in the resultant dental amalgam, whereby less than optimum mechanical properties are obtained. On the other hand, amounts of the non-amalgamatable powder in excess of about 45% of the powder blend are undesirable due to the proportionate decrease in the volume of the continuous phase or matrix produced during the amalgamation reaction between mercury and the amalgamatable powder constituent, which also detracts from obtaining optimum mechanical properties. It is for this reason that the proportion of the non-amalgamatable powder is controlled within the aforementioned range in further consideration of the amount of mercury to be employed in the trituration of a powder mixture with best results usually being achieved when the concentration of the non-amalgamatable powder is controlled within a range of about 25% to about 35% of the powder mixture.

Regardless of the specific composition of the non-amalgamatable alloy powder, the tin constituent is a critical alloying element for achieving the benefits of the present invention. Amounts of tin less than about 1% are generally undesirable because of the marginal improvement achieved in the resistance to deterioration of the powder blend over prolonged periods of storage prior to amalgamation. On the other hand, quantities of tin in excess of about 20% are undesirable due to the increased susceptibility of the powder particles to amalgamation at such high tin contents. Generally, the control of the tin content within a range of about 2% to about 10% provides for almost indefinite shelf life of the powder blend without any noticeable deterioration and further assures the attainment of high strength bonds between the non-amalgamatable particles and the amalgamated silver-mercury matrix without and discernible formation of voids, cracks or pores adjacent to the surfaces of the non-amalgamatable particles. While the particular mechanism by which the controlled addition of tin to the non-amalgamatable alloy powder effects an improvement in the shelf life of the powder mixture and in the resultant amalgams produced therefrom is not completely understood at the present time, it is believed that the addition of controlled quantities of tin aids in the bonding or alloying of the non-amalgamatable particles to the continuous matrix which in essence comprises an amalgam of silver and mercury. The tin constituent is also believed to prevent deterioration of the powder particles over prolonged storage and because of its greater solubility in mercury in comparison to copper, for example, further enhances chemical bonding of the discrete particle phases to the substantially continuous amalgam matrix.

Trituration of the powder mixture with from about 40% up to about 60% mercury, and preferably about 46% to about 50% mercury, is performed in accordance with well known and accepted dental practices. The resultant amalgam hardens within several minutes and the amalgamation reaction is substantially complete after a period of about 24 hours. The resultant amalgams attain their maximum strength after aging for a period of about seven days.

In accordance with the foregoing, the amalgamation of a powder mixture containing from 10% up to 45% of the non-amalgamatable powder with mercury produces a resultant amalgam comprised of from about 40% up to 60% mercury, from about 22% to about 54% of the amalgamatable powder which, in combination with the mercury constituent, defines a continuous matrix of intermetallic compounds of mercury and silver, and lesser quantities of intermetallic compounds of tin, copper and zinc, if present, comprising the continuous phase of amalgam, and about 4% up to about 20% of the non-amalgamatable particles interdispersed through the continuous phase as discrete discontinuous phases of the non-amalgamatable powder particles. When the mercury content is controlled within the preferred range of about 46% up to about 50% of the amalgam, the concentration of the amalgamatable powder in the form of the continuous amalgam phase ranges from about 27.5% up to 48.6%, while the discrete discontinuous phase of non-amalgamatable powder particles ranges from about 5% up to about 24.5%.

In order to further illustrate the improved dental amalgam of the present invention, the following example and comparative data are provided. It will be understood that the example is included for illustrative purposes and is not intended to be limiting of the scope of the present invention as herein described and as set forth in the subjoined claims.

EXAMPLE

Three silver-base alloy powders having an average particle size of 25 microns were prepared by gas atomization. The nominal composition of these powder samples, designated as A, B and C, are set forth in Table 1:

TABLE 1

| Sample | Alloy Powder Composition | | |
|---|---|---|---|
| | Silver | Tin | Copper |
| A | 70.5 | 27.0 | 2.5 |
| B | 72.0 | 0 | 28.0 |
| C | 69.0 | 4.4 | 26.6 |

The composition of sample A is typical of an amalgamatable powder composition. The composition of sample B is typical of a non-amalgamatable powder in accordance with prior art teachings. The composition of sample C is typical of a non-amalgamatable powder containing a controlled quantity of tin in a silver-copper eutectic alloy in accordance with a preferred practice of the present invention.

A powder mixture was prepared employing two parts by weight of sample A and one part by weight of sample B, designated as mixture D, which corresponds to a powder blend prepared in accordance with prior art teachings as set forth in U.S. Pat. No. 3,305,356. A second powder blend, designated as blend E, was prepared employing two parts by weight of sample A and one part by weight of sample C, corresponding to the improved powder blend in accordance with the teachings of the present invention. While in a new or fresh condition, powder blends D and E were triturated with one part mercury for each part alloyed powder and a resultant mixture was shaped into a test specimen and allowed to set for a period of seven days. The resultant test specimens were subjected to compressive strength evaluations at a testing speed of 0.008 inch per minute. An aliquot portion of blends D and E were allowed to age under storage for an 18-month period, whereafter they similarly were triturated with an equal quantity of mercury and formed into test specimens and were tested after setting for a seven-day period. For comparative purposes, an amalgamated test speciment was also prepared employing equal quantities of mercury and the powder of sample A by itself. The resultant compressive strength of the several test specimens in a new as well as aged condition are set forth in Table 2.

TABLE 2

| Sample | Seven-Day Compressive Strength of Amalgamated Powder | | Standard Dev. |
|---|---|---|---|
| | Condition of Powder | Compressive Strength (psi) | |
| A | — | 57,000 | (2,000) |
| D | New | 67,000 | (3,000) |
| E | New | 67,200 | (1,500) |
| D | 18 Month | 59,200 | (1,900) |
| E | 18 Month | 67,000 | (1,500) |

Data as set forth in Table 2 is based on a series of determinations and the standard deviation for the results obtained is also included in Table 2. As will be noted, the compressive strength of blends D and E in a new condition are substantially identical. However, after aging for 18 months, blend D corresponding to the prior art composition, decreased approximately 8,000 psi in compressive strength approaching the compressive strength obtained on sample A. Blend E, on the other hand, after an 18-month aging period prior to amalgamation, exhibited a compressive strength substantially identical to that obtained on the freshly-prepared amalgam employing the same material. The foregoing test data clearly substantiate the improved shelf life and stability of alloy powder mixtures in accordance with the present invention.

While the tensile strength of amalgams have been shown to have little clinical correlation, tensile strength nevertheless is a good indicator of the quality of the bond between the discrete particle phases and the continuous matrix phase. Comparative tensile strength data of amalgams prepared from blends D and E in a new as well as an aged condition are set forth in Table 3.

TABLE 3

| Sample | Seven-Day Tensile Strength of Amalgamated Powder Samples | | Standard Dev. |
|---|---|---|---|
| | Condition of Powder | Tensile Strength (psi) | |
| D | New | 7,200 | (510) |
| E | New | 8,100 | (340) |
| D | 18 Month | 6,600 | (600) |
| E | 18 Month | 7,900 | (350) |

The test data as set forth in Table 3 comprise an average of five tests and the standard deviations for the numerical values given are set forth in the last column thereof. The tensile testing was conducted at a test speed of 0.008 inch per minute on test specimens which had been allowed to set for seven days to attain maximum strength. The higher tensile strength of the amalgam prepared from blend E in comparison to the amalgam prepared from blend D in a new condition clearly evidences the improved bonding between the discrete phases and the continuous matrix of the amalgam of the present invention. This difference is further amplified by the results obtained on the amalgams prepared from the aged powder blends further substantiating the improved shelf life and resistance to deterioration of powder mixtures prepared in accordance with the practice of the present invention.

While it will be apparent that the invention herein described is well calculated to achieve the benefits and advantages as hereinabove set forth, it will be appreciated that the invention is susceptible to modification, variation and change without departing from the spirit thereof.

What is claimed is:

1. A metal powder for use in the preparation of dental restorations and the like by trituration with mercury comprising a mechanical mixture containing about 55% to about 90% of a first powder comprised of a silver-base amalgamatable alloy and about 10% to about 45% of a second powder composed of a substantially non-amalgamatable silver-containing alloy, said first powder consisting essentially of at least about 65% silver, up to about 6% copper, up to about 2% zinc and at least about 25% tin, said second powder consisting essentially of about 1% to about 20% tin, silver as the major alloying agent, and a third alloying constituent individually selected from the group consisting of 5% to 50% cadmium, 5% to 50% zinc, 5% to 50% aluminum, copper in an amount to provide a silver-to-copper ratio of about 2.6:1, up to 30% indium in combination with copper wherein the latter is present in an amount to provide a silver-to-copper ratio of about 2.6:1; said first and said second powder being of an average particle size of less than about 100 microns.

2. The metal powder as defined in claim 1, in which said mechanical mixture contains 65% to 75% of said first powder and 25% to 35% of said second powder.

3. The metal powder as defined in claim 1, in which said first and said second powders are of an average particle size ranging from about 5 microns to about 45 microns.

4. The metal powder as defined in claim 1, wherein the tin content of said second powder ranges from about 2% to about 10%.

5. The metal powder as defined in claim 1, wherein said second powder consists essentially of a eutectic silver-copper alloy having a silver-to-copper ratio of about 2.6:1 containing from 2% up to 20% tin.

6. The metal powder as defined in claim 5, wherein the tin content of said second powder ranges from about 2% to about 10%.

7. A dental amalgam consisting essentially of a continuous matrix composed of an amalgam having dispersed therethrough a plurality of discrete phases chemically bonded by said continuous matrix, said amalgam containing from about 40% to about 60% mercury, from about 22% to about 54% of an amalgamatable alloy powder containing at least about 65% silver, up to about 6% copper, up to about 2% zinc, and greater than about 25% tin; said discrete phases comprising about 4% to about 27% of said amalgam consisting essentially of an alloy containing silver, from about 1% to about 20% tin, and the balance an alloying constituent individually selected from the group consisting of 5% to 50% cadmium, 5% to 50% zinc, 5% to 50% aluminum, copper in an amount to provide a silver-to-copper ratio of about 2.6:1, up to 30% indium in combination with copper wherein the latter is present in an amount to provide a silver-to-copper ratio of about 2.6:1; said discrete phases being of a size less than about 100 microns.

* * * * *